(12) United States Patent
Hart et al.

(10) Patent No.: US 10,792,090 B2
(45) Date of Patent: Oct. 6, 2020

(54) SURGICAL FORCEPS

(71) Applicant: COVIDIEN LP, Mansfield, MA (US)

(72) Inventors: Keir Hart, Lafayette, CO (US); Mark J. Huseman, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 465 days.

(21) Appl. No.: 15/469,675

(22) Filed: Mar. 27, 2017

(65) Prior Publication Data

US 2017/0196619 A1 Jul. 13, 2017

Related U.S. Application Data

(62) Division of application No. 14/176,341, filed on Feb. 10, 2014, now Pat. No. 9,622,810.
(Continued)

(51) Int. Cl.
*A61B 18/12* (2006.01)
*A61B 18/14* (2006.01)
(Continued)

(52) U.S. Cl.
CPC ...... *A61B 18/1442* (2013.01); *A61B 17/2804* (2013.01); *A61B 17/2833* (2013.01);
(Continued)

(58) Field of Classification Search
CPC ............ A61B 17/2804; A61B 17/2833; A61B 17/2841; A61B 17/2909; A61B 17/3201;
(Continued)

(56) References Cited

U.S. PATENT DOCUMENTS 2,198,539 A * 4/1940 Klopfer ................. B26B 13/005
30/161
3,046,655 A * 7/1962 Sproson .................. B26B 13/20
30/233
(Continued)

FOREIGN PATENT DOCUMENTS

CN 201299462 9/2009
DE 2415263 A1 10/1975
(Continued)

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
(Continued)

*Primary Examiner* — Daniel W Fowler
(74) *Attorney, Agent, or Firm* — Carter, DeLuca & Farrell LLP

(57) ABSTRACT

A surgical forceps includes a first shaft member including a proximal portion having a handle at a proximal end thereof and a distal portion having a jaw member at a distal end thereof. The proximal and distal portions are pivotable between an aligned position and an angled position. A second shaft member includes a jaw member at a distal end thereof and a handle at a proximal end thereof. The shaft members are pivotable relative to one another between a spaced-apart position and an approximated position for moving the jaw members relative to one another between an open position and a closed position to grasp tissue therebetween. The proximal portion of the first shaft member is pivoted relative to the distal portion of the first shaft member from the aligned position to the angled position upon movement of the first and second shaft members towards the spaced-apart position.

18 Claims, 8 Drawing Sheets

Related U.S. Application Data

(60) Provisional application No. 61/822,047, filed on May 10, 2013.

(51) Int. Cl.
*A61B 17/28* (2006.01)
*A61B 34/00* (2016.01)
*A61B 17/00* (2006.01)
*A61B 18/00* (2006.01)
*A61B 90/00* (2016.01)

(52) U.S. Cl.
CPC .......... *A61B 17/2841* (2013.01); *A61B 34/76* (2016.02); *A61B 2017/00424* (2013.01); *A61B 2018/00922* (2013.01); *A61B 2018/1455* (2013.01); *A61B 2090/065* (2016.02)

(58) Field of Classification Search
CPC .............. A61B 17/295; A61B 18/1442; A61B 2018/1462; A61B 2018/146
See application file for complete search history.

(56) References Cited

U.S. PATENT DOCUMENTS

| | | |
|---|---|---|
| 3,599,516 A | 8/1971 | Smedley |
| 4,088,134 A | 5/1978 | Mazzariello |
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,207,702 A | 5/1993 | Pearl |
| D343,453 S | 1/1994 | Noda |
| 5,281,220 A * | 1/1994 | Blake, III .............. A61B 17/29 606/113 |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,658,281 A | 8/1997 | Heard |
| D384,413 S | 9/1997 | Zlock et al. |
| 5,693,069 A | 12/1997 | Shallman |
| H001745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| 6,102,909 A | 8/2000 | Chen et al. |
| H001904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H002037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,303,586 B2 | 11/2012 | Cunningham et al. |
| 8,628,557 B2 | 1/2014 | Collings et al. |
| 8,663,270 B2 | 3/2014 | Donnigan et al. |
| RE44,834 E | 4/2014 | Dumbauld et al. |
| 2002/0023302 A1 | 2/2002 | Montague et al. |
| 2003/0199869 A1 | 10/2003 | Johnson et al. |
| 2007/0022849 A1 | 2/2007 | Poehlmann |
| 2007/0199198 A1 | 8/2007 | Hsieh |
| 2008/0033428 A1 | 2/2008 | Artale et al. |
| 2008/0215048 A1 | 9/2008 | Hafner et al. |
| 2009/0158598 A1 * | 6/2009 | Ishida .................... B26B 13/20 30/232 |
| 2010/0064862 A1 * | 3/2010 | Fournier ................ A01K 97/00 81/415 |
| 2011/0016728 A1 * | 1/2011 | Hann ..................... B26B 13/12 30/232 |
| 2011/0162796 A1 | 7/2011 | Guerra |
| 2012/0083786 A1 * | 4/2012 | Artale ................ A61B 18/1442 606/51 |
| 2013/0023917 A1 * | 1/2013 | Cruz Hernandez .... A61B 17/28 606/174 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |

(56) References Cited

FOREIGN PATENT DOCUMENTS

| | | |
|---|---|---|
| JP | 6-511401 | 12/1994 |
| JP | 06343644 A | 12/1994 |
| JP | 07265328 A | 10/1995 |
| JP | 08056955 | 3/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 09000538 A | 1/1997 |
| JP | 09010223 | 1/1997 |
| JP | 9-122138 A | 5/1997 |
| JP | 0010000195 A | 1/1998 |
| JP | H10-24051 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 A2 | 6/2002 |
| WO | 2006021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

"Electrosurgery: A Historical Overview" Innovations in Electrosurgery; Sales/Product Literature; Dec. 31, 2000.
W. Scott Helton, "LigaSure Vessel Sealing System: Revolutionary Hemostasis Product for General Surgery"; Sales/Product Literature 1999.
Levy et al., "Update on Hysterectomy—New Technologies and Techniques" OBG Management, Feb. 2003.
Sengupta et al., "Use of a Computer-Controlled Bipolar Diathermy System in Radical Prostatectomies and Other Open Urological Surgery" ANZ Journal of Surgery (2001) 71.9 pp. 538-540.
Peterson et al. "Comparison of Healing Process Following Ligation with Sutures and Bipolar Vessel Sealing" Surgical Technology International (2001).
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
LigaSure Vessel Sealing System, the Seal of Confidence in General, Gynecologic, Urologic, and Laparaoscopic Surgery; Sales/Product Literature; Apr. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Rothenberg et al. "Use of the LigaSure Vessel Sealing System in Minimally Invasive Surgery in Children" Int'l Pediatric Endosurgery Group (IPEG) 2000.
McLellan et al. "Vessel Sealing for Hemostasis During Gynecologic Surgery" Sales/Product Literature 1999.
Kennedy et al. "High-burst-strength, feedback-controlled bipolar vessel sealing" Surgical Endoscopy (1998) 12: 876-878.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Johnson et al. "Evaluation of the LigaSure Vessel Sealing System in Hemorrhoidectormy" American College of Surgeons (ACS) Clinicla Congress Poster (2000).
Carus et al., "Initial Experience With The LigaSure Vessel Sealing System in Abdominal Surgery" Innovations That Work,.quadrature. Jun. 2002.
Barbara Levy, "Use of a New Vessel Ligation Device During Vaginal Hysterectomy" FIGO 2000, Washington, D.C.
Joseph Ortenberg "LigaSure System Used in Laparoscopic 1st and 2nd Stage Orchiopexy" Innovations That Work, Nov. 2002.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Crawford et al. "Use of the LigaSure Vessel Sealing System in Urologic Cancer Surgery" Grand Rounds in Urology 1999 vol. 1 Issue 4 pp. 10-17.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
"Reducing Needlestick Injuries in the Operating Room" Sales/Product Literature 2001.

(56) References Cited

OTHER PUBLICATIONS

E. David Crawford "Use of a Novel Vessel Sealing Technology in Management of the Dorsal Veinous Complex" Sales/Product Literature 2000.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Bergdahl et al. "Studies on Coagulation and the Development of an Automatic Computerized Bipolar Coagulator" J. Neurosurg, vol. 75, Jul. 1991, pp. 148-151.

Levy et al. "Use of a New Energy-based Vessel Ligation Device During Vaginal Hysterectomy" Int'l Federation of Gynecology and Obstetrics (FIGO) World Congress 1999.

Seyfan et al. "Sutureless Closed Hemorrhoidectomy: A New Technique" Annals of Surgery vol. 234 No. 1, Jul. 2001 pp. 21-24.

Michael Choti, "Abdominoperineal Resection with the LigaSure Vessel Sealing System and LigaSure Atlas 20 cm Open Instrument" Innovations That Work, .quadrature.Jun. 2003.

Muller et al., "Extended Left Hemicoletomy Using the LigaSure Vessel Sealing System" Innovations That Work,.quadrature.Sep. 1999.

Olsson et al. "Radical Cystectomy in Females" Current Surgical Techniques in Urology, vol. 14, Issue 3.

Jarrett et al., "Use of the LigaSure Vessel Sealing System for Perl-Hilar Vessels in Laparoscopic Nephrectomy" Sales Product Literature.

Craig Johnson. "Use of the LigaSure Vessel Sealing System in Bloodless Hemorrhoidectomy" That Work, Mar. 2000.

Koyle et al., "Laparoscopic Palomo Varicocele Ligation in Children and Adolescents" Pediatric Endosurgery & Innovative Techniques, vol. 6, No. 1, 2002.

U.S. Appl. No. 08/926,869, filed Sep. 10, 1997; inventor: James G. Chandler.

U.S. Appl. No. 09/177,950, filed Oct. 23, 1998; inventor: Randel A. Frazier.

U.S. Appl. No. 09/387,883, filed Sep. 1, 1999; inventor: Schmaltz.

U.S. Appl. No. 09/591,328, filed Jun. 9, 2000; inventor: Ryan.

U.S. Appl. No. 12/336,970, filed Dec. 17, 2008; inventor: Sremcich.

U.S. Appl. No. 13/731,674, filed Dec. 31, 2012; inventor: Siebrecht.

\* cited by examiner

SURGICAL FORCEPS

CROSS-REFERENCE TO RELATED APPLICATION

This application is a divisional application of U.S. application Ser. No. 14/176,341, filed on Feb. 10, 2014, which claims the benefit of and priority to U.S. Provisional application Ser. No. 61/822,047, filed on May 10, 2013, the entire contents of each of which are incorporated herein by reference.

BACKGROUND

Technical Field

The present disclosure relates to surgical devices and, more particularly, to hemostat-style surgical forceps for grasping, treating, and cutting tissue.

Background of Related Art

A surgical forceps is a plier-like device which relies on mechanical action between its jaws to grasp, clamp, and constrict tissue. Energy-based surgical forceps utilize both mechanical clamping action and energy to affect hemostasis by heating tissue to coagulate and/or cauterize tissue. Certain surgical procedures require more than simply cauterizing tissue and rely on the unique combination of clamping pressure, precise energy control and gap distance (i.e., distance between opposing jaw members when closed about tissue) to "seal" tissue. Typically, once tissue is sealed, the surgeon has to accurately sever the tissue along the newly formed tissue seal. Accordingly, many tissue sealing devices have been designed which incorporate a knife or blade member which effectively severs the tissue after forming a tissue seal. More recently, tissue sealing devices have incorporated energy-based cutting features for energy-based tissue division.

With respect to hemostat-style surgical forceps for use in relatively deep openings and/or in confined spaces, longer shaft members provide the surgeon with the ability to reach the target tissue. However, as the lengths of the shaft members increase, so does the range of motion required to open and close the jaw members.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with aspects of the present disclosure, a surgical forceps is provided. the surgical forceps includes a first shaft member and a second shaft member. The first shaft member includes a proximal portion having a handle disposed at a proximal end thereof, and a distal portion having a jaw member disposed at a distal end thereof. The proximal and distal portions are pivotably coupled to one another and are pivotable relative to one another between an aligned position, wherein the proximal and distal portions cooperate to define a substantially linear configuration, and an angled position, wherein the proximal portion is angled relative to the distal portion. The second shaft member includes a jaw member disposed at a distal end thereof and a handle disposed at a proximal end thereof. The first and second shaft members are pivotably coupled to one another towards the distal end of the distal portion of the first shaft member and the distal end of the second shaft member and are pivotable relative to one another between a spaced-apart position and an approximated position for moving the jaw members relative to one another between an open position and a closed position to grasp tissue therebetween. The proximal portion of the first shaft member is pivoted relative to the distal portion of the first shaft member from the aligned position to the angled position upon movement of the first and second shaft members towards the spaced-apart position.

In an aspect of the present disclosure, in the angled position, the proximal portion of the first shaft member is angled towards the second shaft member to decrease a distance between the handles of the first and second shaft members.

In another aspect of the present disclosure, a stop member is disposed on one of the proximal and distal portions of the first shaft member. The stop member is configured to inhibit pivoting of the proximal portion away from the second shaft member beyond the aligned position.

In yet another aspect of the present disclosure, each of the handles defines a finger hole therethrough.

In still another aspects of the present disclosure, a locking mechanism is disposed on the first shaft member. The locking mechanism is configured to selectively lock the proximal and distal portions of the first shaft member in the aligned position.

In still yet another aspect of the present disclosure, one or both of the jaw members is adapted to connect to a source of energy for conducting energy through tissue grasped between the jaw members to treat tissue. In such aspects, one of the shaft members may further include an activation button positioned to oppose the other shaft member such that energy is supplied to the at least one jaw member upon movement of the shaft members to the approximated position.

In accordance with aspects of the present disclosure, another surgical forceps is provided that include a first jaw member having a distal jaw body and a proximal jaw flange extending proximally from the distal jaw body. The proximal jaw flange includes an extension portion having a transverse pin extending therethrough. A first shaft member is also provided. The first shaft member has a handle disposed at a proximal end thereof and includes a distal end defining an opening and one or more slots adjacent the opening. The extension portion of the proximal jaw flange extends into the opening and the transverse pin is disposed within the slot(s). The transverse pin is movable from a first end of the slot(s), wherein the first shaft member and the extension portion cooperate to define a substantially linear configuration, to a second end of the slot(s), wherein the first shaft member is angled relative to the extension portion. A second shaft member including a jaw member disposed at a distal end thereof and a handle disposed at a proximal end thereof is also provided. The jaw member of the second shaft member is pivotably coupled to the jaw member of the first shaft member. The first and second shaft members are pivotable relative to one another between a spaced-apart position and an approximated position for moving the jaw members relative to one another between an open position and a closed position to grasp tissue therebetween. The first shaft member is moved from the first end of the slot(s) towards the second end of the slot(s) upon movement of the first and second shaft members towards the spaced-apart position.

In an aspect of the present disclosure, in the angled position, the handle of the first shaft member is angled towards the second shaft member to decrease a distance between the handles of the first and second shaft members.

In another aspect of the present disclosure, each of the handles defines a finger hole therethrough.

In yet another aspect of the present disclosure, a linkage is coupled between the first and second shaft members. In such aspects, the linkage may be pivotably coupled to one of the shaft members and coupled to the other shaft member via a slot-pin engagement. Further still, the linkage may be configured such that, in the approximated position of the shaft members, the linkage is disposed in an angled position, and such that, in the spaced-apart position of the shaft members, the linkage is disposed in a substantially vertical position.

In still another aspect of the present disclosure, one or both of the jaw members is adapted to connect to a source of energy for conducting energy through tissue grasped between the jaw members to treat tissue. In such aspects, one of the shaft members may further include an activation button positioned to oppose the other shaft member such that energy is supplied to the at least one jaw member upon movement of the shaft members to the approximated position.

In accordance with aspects of the present disclosure, another surgical forceps is provided that includes first and second shaft members, each including a jaw member disposed at a distal end thereof and a handle disposed at a proximal end thereof. The first and second shaft members are pivotably coupled to one another towards the distal ends thereof and are pivotable relative to one another between a spaced-apart position and an approximated position for moving the jaw members relative to one another between an open position and a closed position to grasp tissue therebetween. The handles of the first and second shaft members extend inwardly towards one another and are longitudinally offset relative to one another.

In an aspect of the present disclosure, each shaft member defines an outer dimension along an outwardly-facing side thereof. The handles of the respective shaft members are fully disposed within the respective outer dimensions.

In another aspect of the present disclosure, one of the shaft members defines a recess configured to at least partially receive the handle of the other shaft member upon movement of the shaft members to the approximated position.

In yet another aspect of the present disclosure, one or both of the jaw members is adapted to connect to a source of energy for conducting energy through tissue grasped between the jaw members to treat tissue. In such aspects, one of the shaft members may further include an activation button positioned to oppose the other shaft member such that energy is supplied to the at least one jaw member upon movement of the shaft members to the approximated position.

BRIEF DESCRIPTION OF THE DRAWINGS

Various aspects and features of the present disclosure are described herein with reference to the drawings wherein.

DETAILED DESCRIPTION

Figure 1A:
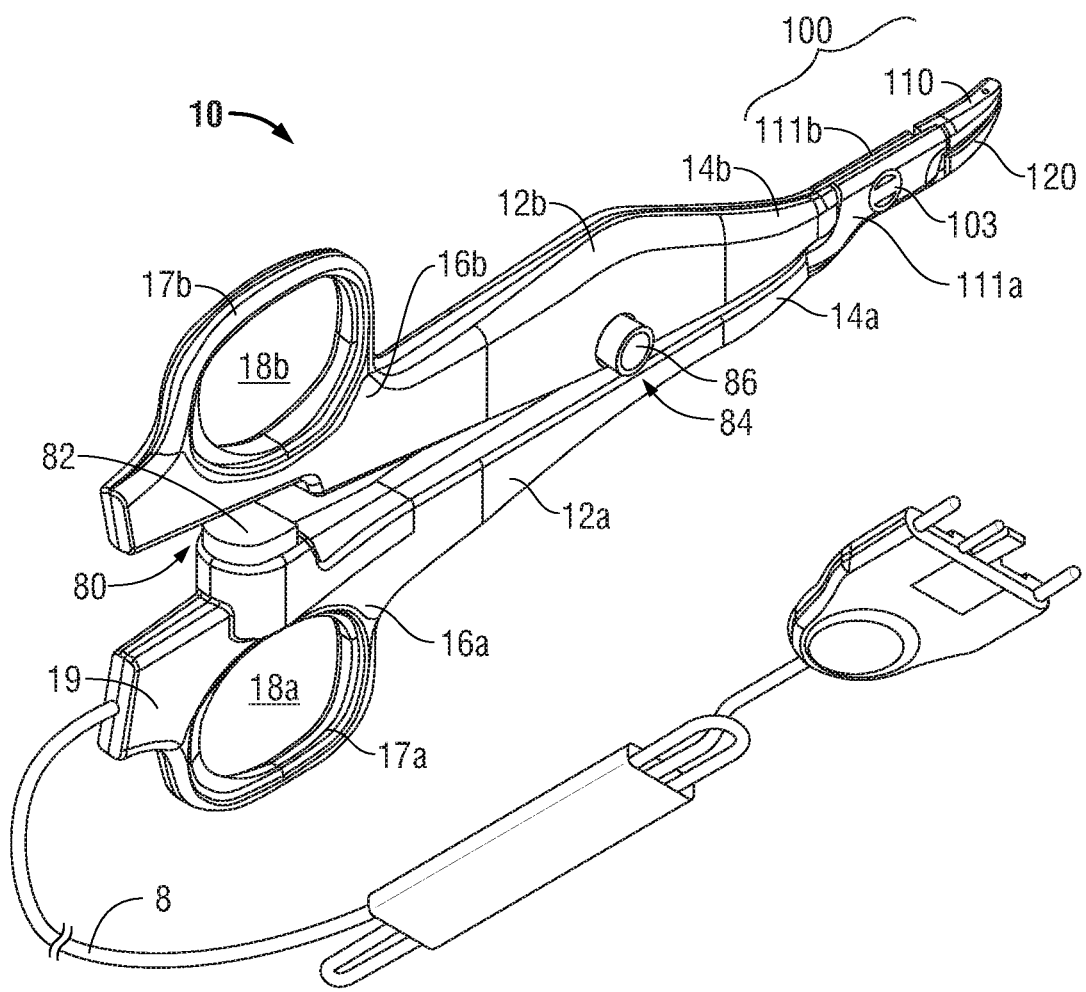
FIG. 1A is a perspective view of a forceps provided in accordance with the present disclosure, configured for grasping, treating, and electrically cutting tissue.
Figure 1B:
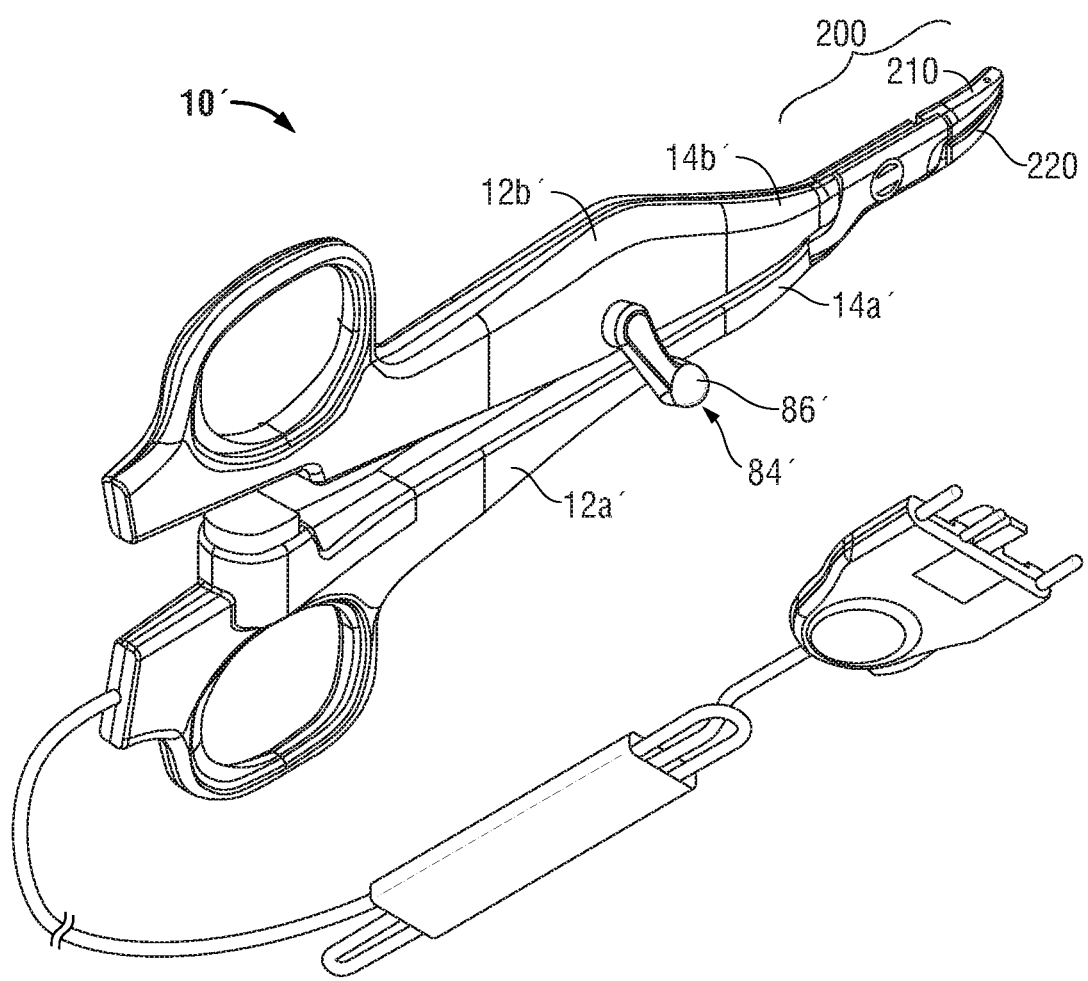
FIG. 1B is a perspective view of another forceps provided in accordance with the present disclosure, configured for grasping, treating, and mechanically cutting tissue.

Turning to FIGS. 1A and 1B, two embodiments of hemostat-style surgical forceps configured for use in accordance with the present disclosure in a variety of surgical procedures are shown generally identified by reference numerals 10 and 10', respectively, although it is contemplated that any other suitable surgical device may be utilized in accordance with the present disclosure. Obviously, different electrical and mechanical connections and considerations apply to each particular type of device, however, the aspects and features of the present disclosure remain generally consistent regardless of the particular device used.

Referring to FIG. 1A, forceps 10 is shown including two elongated shaft members 12a and 12b each having a distal end 14a and 14b and a proximal end 16a and 16b, respectively. End effector assembly 100, including opposing jaw members 110, 120, is attached to distal ends 14a and 14b of shaft members 12a and 12b, respectively. A pivot pin 103 is interdisposed between shaft members 12a, 12b and the respective jaw members 110, 120 thereof such that shaft members 12a, 12b may be pivoted relative to one another between a spaced-apart position and an approximated position to effect movement of jaw members 110, 120 relative to one another between an open position and a closed position, respectively, for grasping tissue therebetween.

Each shaft member 12a, 12b includes a handle 17a, 17b disposed at the proximal end 16a, 16b thereof. Each handle 17a, 17b defines a finger hole 18a, 18b therethrough for receiving a finger of the user. As can be appreciated, finger holes 18a, 18b facilitate movement of shaft members 12a, 12b relative to one another to, in turn, pivot jaw members 110, 120 from the open position to the closed position for grasping tissue therebetween.

One of shaft members 12a, 12b, e.g., shaft member 12a, includes a proximal shaft connector 19 configured to connect forceps 10 to a source of energy, e.g., a generator (not shown). Proximal shaft connector 19 secures a cable 8 to forceps 10 such that the user may selectively supply energy, e.g., electrosurgical energy, to jaw members 110, 120 for treating, e.g., sealing, tissue and for energy-based tissue cutting. More specifically, a first activation assembly 80 is provided for supplying energy to jaw members 110, 120 to treat tissue upon sufficient approximation of shaft members 12a, 12b, e.g., upon activation of activation button 82 via shaft member 12b. A second activation assembly 84 including a selectively depressible activation button 86 is provided one of the shaft members 12a, 12b, e.g., shaft member 12b, for selectively supplying energy, e.g., electrosurgical energy, to either or both of jaw members 110, 120 for energy-based tissue cutting.

Figure 2A:
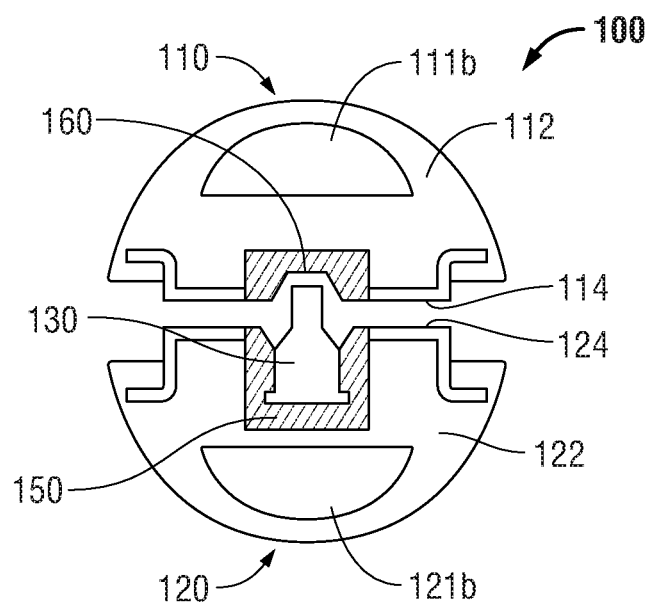
FIG. 2A is a transverse, cross-sectional view of the end effector assembly of the forceps of FIG. 1A.

With additional reference to FIG. 2A, end effector assembly 100 of forceps 10 includes first and second jaw members 110, 120, each including a proximal flange portion 111a, 121a, a distal jaw portion 111b, 121b, an outer insulative jaw housing 112, 122, and a tissue-contacting plate 114, 124, respectively. Proximal flange portions 111a, 121a of jaw members 110, 120 are pivotably coupled to one another about pivot pin 103 for moving jaw members 110, 120 between the open and closed positions upon movement of shaft members 12a, 12b between the spaced-apart and approximated positions. Proximal flange portions 111a, 121a may be fixedly engaged, integrally formed, releasably engaged, or otherwise or secured to respective shaft members 12a, 12b. Distal jaw portions 111b, 121b of jaw members 110, 120 are configured to support jaw housings 112, 122, and tissue-contacting plates 114, 124, respectively, thereon. Further, one of the jaw members 110, 120, e.g., jaw members 120, includes an energy-based cutting member 130 disposed thereon, as will be described in greater detail below.

Tissue-contacting plates 114, 124 are formed from an electrically conductive material, e.g., for conducting electrical energy therebetween for treating tissue, although tissue-contacting plates 114, 124 may alternatively be configured to conduct any suitable energy through tissue grasped therebetween for energy-based tissue treatment, e.g., tissue sealing. Energy-based cutting member 130 is likewise formed from an electrically conductive material, e.g., for conducting electrical energy between energy-based cutting member 130 and one or both of tissue-contacting plates 114, 124 for electrically cutting tissue, although energy-based cutting member 130 may alternatively be configured to conduct any suitable energy through tissue for electrically cutting tissue.

Tissue-contacting plates 114, 124 are coupled to activation switch 82 and the source of energy (not shown) such that energy, e.g., electrosurgical energy, may be selectively supplied to tissue-contacting plate 114 and/or tissue-contacting plate 124 and conducted therebetween and through tissue disposed between jaw members 110, 120 to treat, e.g., seal, tissue in a first mode of operation. Likewise, cutting member 130 is similarly coupled to activation switch 86 and the source of energy (not shown) such that energy, e.g., electrosurgical energy, may be selectively supplied to cutting member 130 and conducted through tissue disposed between jaw members 110, 120 to either or both of tissue-contacting plates 114, 124 to cut tissue in a second mode of operation. A first insulating member 150 surrounds cutting member 130 to insulate tissue-contacting plate 124 and cutting member 130 from one another. A second insulating member 160 disposed within a longitudinal slot defined within tissue-contacting plate 114 of jaw member 110 opposes cutting member 130 to insulate cutting member 130 from tissue-contacting plate 114 of jaw member 110 when jaw members 110, 120 are disposed in the approximated position.

Turning to FIG. 1B, forceps 10' is similar to forceps 10 (FIG. 1A) and, thus, only the differences therebetween will be described in detail below for purposes of brevity. Forceps 10' generally includes two elongated shaft members 12a' and 12b' and an end effector assembly 200 including opposing jaw members 210, 220 attached at distal ends 14a' and 14b' of shaft members 12a', 12b'. One of the shaft members 12a', 12b', e.g., shaft member 12b', further includes a trigger assembly 84' including a selectively actuatable trigger 86' operably coupled to a cutting member 230 (FIG. 2B) for selectively advancing cutting member 230 (FIG. 2B) between jaw members 210, 220 to cut tissue grasped therebetween. That is, forceps 10' differs from forceps 10 (FIG. 1A) in that forceps 10' is configured for mechanical tissue cutting, while forceps 10 (FIG. 1A) is configured for electrical tissue cutting.

Figure 2B:
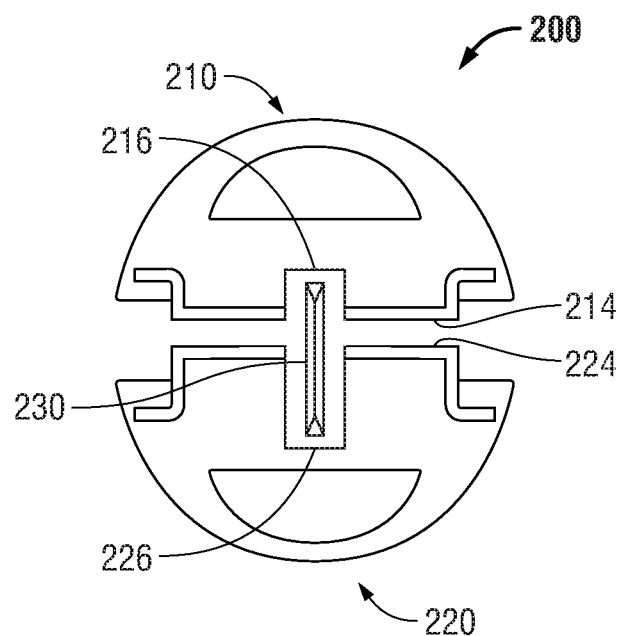
FIG. 2B is a transverse, cross-sectional view of the end effector assembly of the forceps of FIG. 1B.

With additional reference to FIG. 2B, end effector assembly 200 of forceps 10' is similar to end effector assembly 100 of forceps 10 (see FIGS. 1A and 2A) and may include any of the features of end effector assembly 100 (FIG. 2A), except where specifically contradicted below. End effector assembly 200 includes first and second jaw members 210, 220, each including a tissue-contacting plate 214, 224 and a longitudinally-extending slot 216, 226, respectively. A cutting member 230 is configured for longitudinal translation through slots 216, 226 of jaw members 210, 220, e.g., upon activation of trigger 86', to mechanically cut tissue grasped between jaw members 210, 220.

Turning now to FIGS. 3A-5, various embodiments of shaft members and/or shaft assemblies configured for use with forceps similar to forceps 10, 10' (FIGS. 1A and 1B, respectively), are described in detail below. The various embodiments detailed below may include any of the features of forceps 10, 10' (FIGS. 1A and 1B, respectively). Further, to the extent consistent, any of the embodiments detailed below may include any or all of the features of any of the other embodiments detailed below. For the purposes of brevity, similar features described above with respect to forceps 10, 10' (FIGS. 1A and 1B, respectively) or any of the other embodiments detailed herein will only be summarily described or omitted entirely.

The various embodiments of forceps described hereinbelow are particularly useful for surgical procedures requiring the surgeon to grasp, treat, and/or cut tissue positioned within deep openings and/or in confined spaces, although these forceps are similarly advantageous for grasping, treating, and/or cutting tissue in a variety of other surgical procedures. More specifically, the presently disclosed embodiments of forceps include shaft members having increased lengths and/or extended shaft assemblies, while also including components and/or features that account for the increased range of motion requirements for opening and closing jaw members associated with such increased length shafts and/or extended shaft assemblies.

Figure 3A:
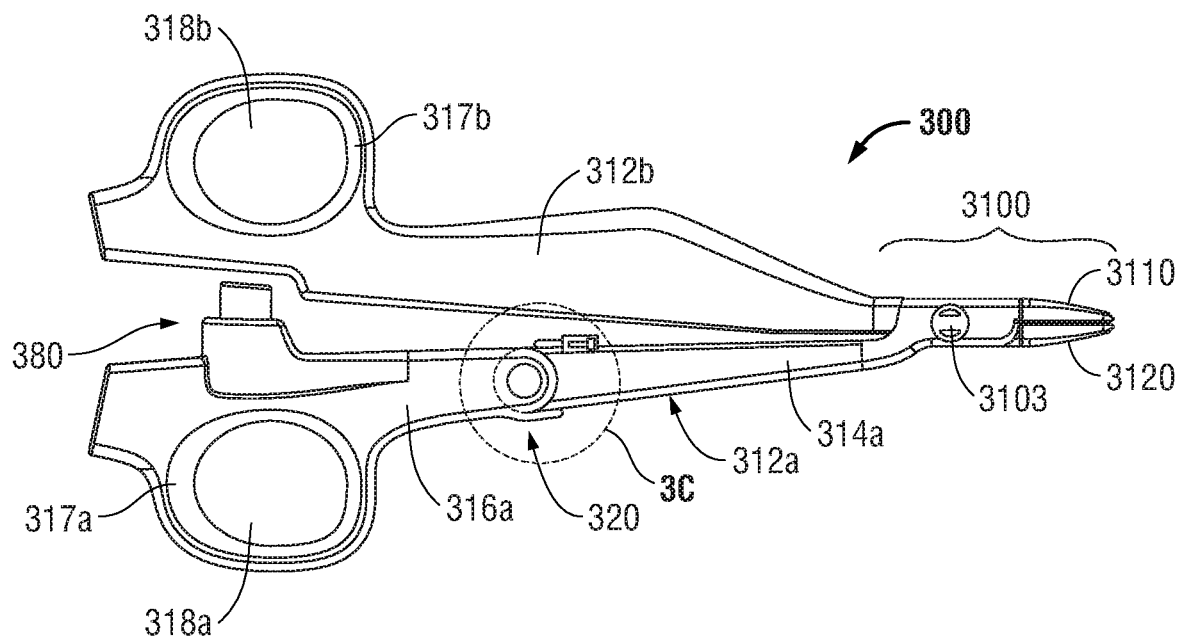
FIG. 3A is a side view of another forceps provided in accordance with the present disclosure, wherein jaw members of the end effector assembly of the forceps are disposed in a closed position.
Figure 3B:
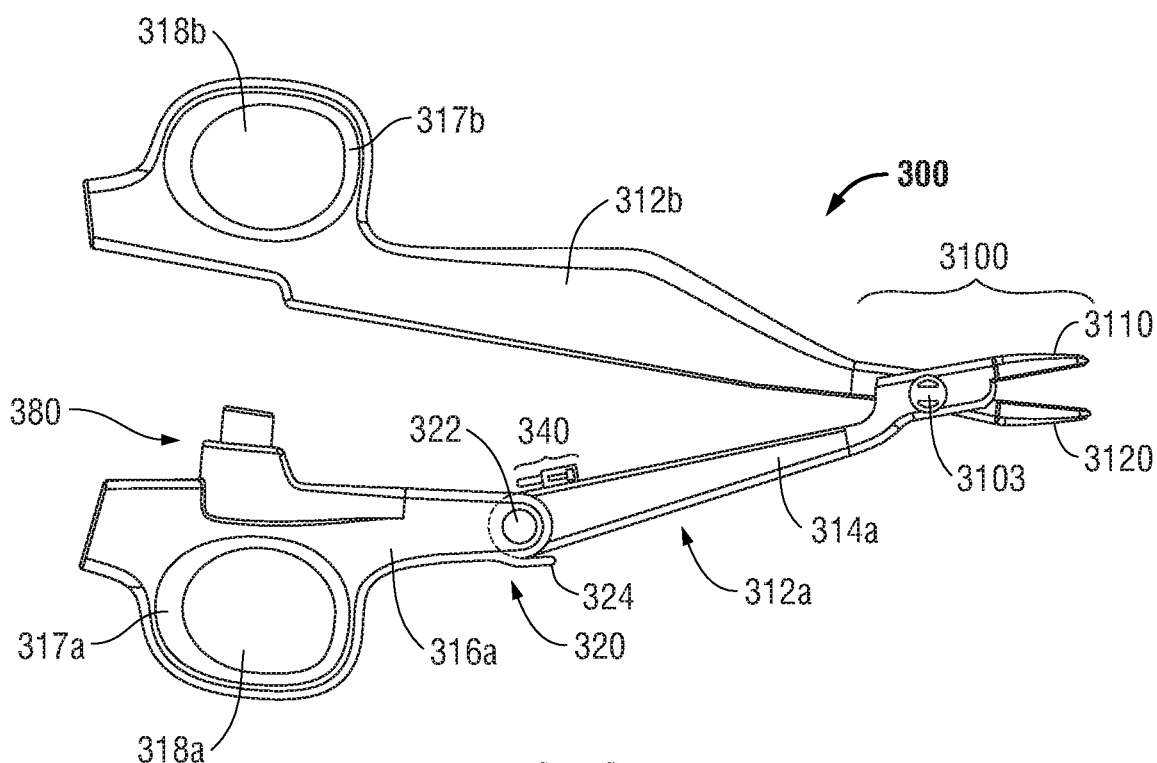
FIG. 3B is a side view of the forceps of FIG. 3A, wherein the jaw members are disposed in an open position.
Figure 3C:
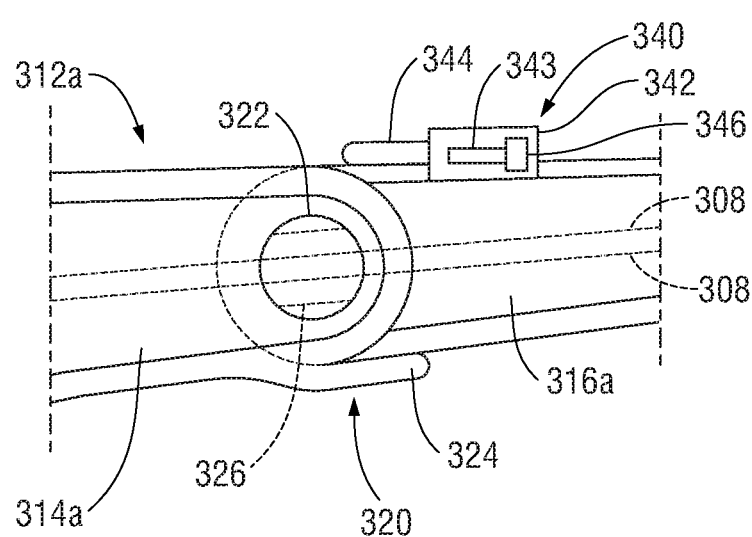
FIG. 3C is an enlarged view of the area of detail indicated as "3C" in FIG. 3A.

Referring to FIGS. 3A-3C, another embodiment of a forceps provided in accordance with the present disclosure is shown generally identified by reference numeral 300. Forceps 300 is shown generally including a pair of elongated shaft members 312a and 312b an end effector assembly 3100 having first and second jaw members 3110, 3120, disposed at the distal ends of shaft members 312a, 312b. Similarly as described above, a pivot pin 3103 pivotably couples shaft members 312a, 312b and, thus, the jaw members 3110, 3120 thereof such that shaft members 312a, 312b may be pivoted relative to one another between a spaced-apart position and an approximated position to effect movement of jaw members 3110, 3120 relative to one another between an open position and a closed position, respectively, for grasping tissue therebetween.

One or both of the shaft members 312a, 312b, e.g., shaft member 312a, includes a distal portion 314a and a proximal portion 316a that are interconnected via a pivot assembly 320. Distal portion 314a includes jaw member 3110 disposed at the distal end thereof and is pivotably coupled to shaft member 312b via pivot pin 3103. Proximal portion 316a includes a handle 317a, which defines a finger hole 318a, disposed towards the proximal end thereof and further includes an activation assembly 380 disposed towards the proximal end thereof.

Pivot assembly 320 includes a pivot member 322 that pivotably couples the adjacent ends of distal and proximal portions 314a, 316a, respectively, to one another such that proximal portion 316a may pivot about pivot member 322 and relative to distal portion 314a between an aligned position, wherein shaft member 312a defines a substantially linear configuration with distal and proximal portions 314a, 316a substantially aligned with one another (FIG. 3A), and an angled position, wherein shaft member 312a defines an angled configuration with proximal portion 316a angled towards shaft member 312b and relative to distal portion 314a (FIG. 3B).

With particular reference to FIG. 3C, in conjunction with FIGS. 3A-3B, pivot assembly 320, in some embodiments, further includes a stop member 324 disposed on the adjacent end of either of distal and proximal portions 314a, 316a, e.g., proximal portion 316a, for inhibiting proximal portion 316a from pivoting about pivot member 322 relative to distal portion 314a and away from shaft member 312b beyond the aligned position. Pivot member 322 may also define an internal passage 326 extending therethrough to permit passage of wires 308 between distal and proximal portions 314a, 316a, for coupling the source of energy (not shown) and activation assembly 380 to end effector assembly 3100 (see FIGS. 3A-3B).

In some embodiments, one of the distal and proximal portions 314a, 316a, e.g., distal portion 314a, of shaft member 312a includes a locking mechanism 340 for releasably locking proximal portion 316a in the aligned position. Locking mechanism 340 includes a housing 342 extending from distal portion 314a adjacent pivot assembly 320. Housing 342 slidably receives a locking bar 344. An actuator 346 extends through a slot 343 defined within housing 342 and is coupled to locking bar 344 such that translation of actuator 346 through slot 343 effects movement of locking bar 344 between a retracted position, wherein locking bar 344 is positioned distally of pivot assembly 320, and an extended position, wherein locking bar 344 extends proximally beyond pivot assembly 320 to at least partially overlap proximal portion 316a. As can be appreciated, in the extended position, locking bar 344 and stop member 324 cooperate to substantially inhibit pivoting of proximal portion 316a, thereby retaining proximal portion 316a in the aligned position. Other suitable locking mechanisms 340 are also contemplated.

Forceps 300 is configured to enable full opening of jaw members 3110, 3120 while reducing the range of motion, e.g., the distance between handles 317a, 317b of shaft members 312a, 312b, respectively, required to fully open jaw members 3110, 3120. As detailed above, such a feature is advantageous for use with elongated shaft members, although this feature is also advantageous in other situation, e.g., for surgeons having smaller hands.

Referring still to FIGS. 3A-3C, in use, in order to move jaw members 3110, 3120 to the fully open position, the surgeon, with a finger inserted through each of finger holes 318a, 318b of handles 317a, 317b, respectively, moves shaft members 312a, 312b apart from one another from the approximated position (FIG. 3A) towards the spaced-apart position (FIG. 3B) to pivot jaw members 3110, 3120 from the closed position (FIG. 3A) towards the open position (FIG. 3B). As shaft members 312a, 312b are moved further towards the spaced-apart position, e.g., as handles 317a, 317b are moved further apart from one another, the surgeon's ability to further space-apart shaft members 312a, 312b is constrained by the size of the surgeon's hand and/or the surgeon's ability to spread handles 317a, 317b. However, pivot assembly 320, with locking bar 344 of locking mechanism 340 in the retracted position, allows proximal portion 316a of shaft member 312a to pivot relative to distal portion 314a of shaft member 312a and towards shaft member 312b from the aligned position (FIG. 3A) to the angled position (FIG. 3B) as shaft members 312a, 312b are moved further towards the spaced-apart position, thereby reducing the distance between handles 317a, 317b and facilitating full opening of jaw members 3110, 3120 (FIG. 3B). Where use of pivot assembly 320 is not desired, locking bar 344 of locking mechanism 340 may be moved from the retracted position to the extended position to lock shaft member 312a in the aligned position (FIG. 3A) throughout movement of shaft members 312a, 312b between the spaced-apart and approximated positions.

In order to move jaw members 3110, 3120 to the closed position for grasping tissue therebetween, the surgeon moves shaft members 312a, 312b towards one another. As shaft members 312a, 312b are moved further towards the approximated position, proximal portion 316a of shaft member 312a is pivoted relative to distal portion 314a of shaft member 312 and away from shaft member 312b from the angled position (FIG. 3B) to the aligned position (FIG. 3A) such that shaft members 312a, 312b may be fully approximated and, thus, such that jaw members 3110, 3120 may be fully closed about tissue grasped therebetween. Fully closing jaw members 3110, 3120 about tissue is important in that it has been found that a grasping pressure in the range of about 3 kg/cm² to about 16 kg/cm² and a gap distance of about 0.001 inches to about 0.006 inches between jaw members 3110, 3120 facilitates formation of an effective tissue seal, although other ranges are also contemplated.

Referring to FIGS. 4A-4D, another forceps provided in accordance with the present disclosure is shown generally identified by reference numeral 400. Forceps 400 is shown generally including a pair of elongated shaft members 412a, 412b, and an end effector assembly 4100 having first and second jaw members 4110, 4120, disposed at the distal ends of shaft members 412a, 412b. Similarly as described above, a pivot pin 4103 pivotably couples shaft members 412a, 412b and, thus, the jaw members 4110, 4120 thereof such that shaft members 412a, 412b may be pivoted relative to one another between a spaced-apart position and an approximated position to effect movement of jaw members 4110, 4120 relative to one another between an open position and a closed position, respectively, for grasping tissue therebetween.

One or both of the shaft members 412a, 412b, e.g., shaft member 412a, is movably coupled to its respective jaw member 4110. The other shaft member 412b may likewise be movably coupled to its respective jaw member 4120, or may be fixedly engaged, integrally formed, or otherwise secured thereto. More specifically, proximal flange portion 4111a of jaw member 4110 includes a proximal extension 4112 including a transverse pin 4113 extending from either side thereof. Shaft member 412a defines a opening (not explicitly shown) towards the distal end thereof that is configured to receive proximal extension 4112 of proximal flange portion 4111a of jaw member 4110, and further defines an angled slot 414 on each opposed side wall thereof (only one of which is shown) for receiving the portions of transverse pin 4113 extending from each side of proximal extension 4112. The reverse configuration is also contemplated, e.g., wherein flange portion 4111a of jaw member 4110 defines a pair of slots and wherein shaft member 412a includes a transverse pin extending from both sides thereof and through the slots.

Continuing with reference to FIGS. 4A-4D, forceps 400 further includes a linkage 440 interconnecting shaft members 412a, 412b proximally of pivot pin 4103. Linkage 440 is pivotably coupled to shaft member 412b via a pivot pin 442 and is coupled to shaft member 412a via a slot-pin engagement 444, although this configuration may be reversed. As shaft members 412a, 412b are moved between the spaced-apart and approximated positions to open and close jaw members 4110, 4120, first end 443 of linkage 440 is pivoted about pivot pin 442 relative to shaft member 412b and second end 445 of linkage 440 is both pivoted relative to shaft member 412a and translated along the slot of slot-pin engagement 444 to permit such movement of shaft members 412a, 412b relative to one another. Linkage 440 provides stability and support to shaft members 412a, 412b. However, in some embodiments, linkage 440 is not provided.

Similarly as described above with respect to forceps 300 (FIGS. 3A-3C), forceps 400 is configured to enable full opening of jaw members 4110, 4120 while reducing the range of motion, e.g., the distance between handles 417a, 417b of shaft members 412a, 412b, respectively, required to fully open jaw members 4110, 4120.

Figure 4A:
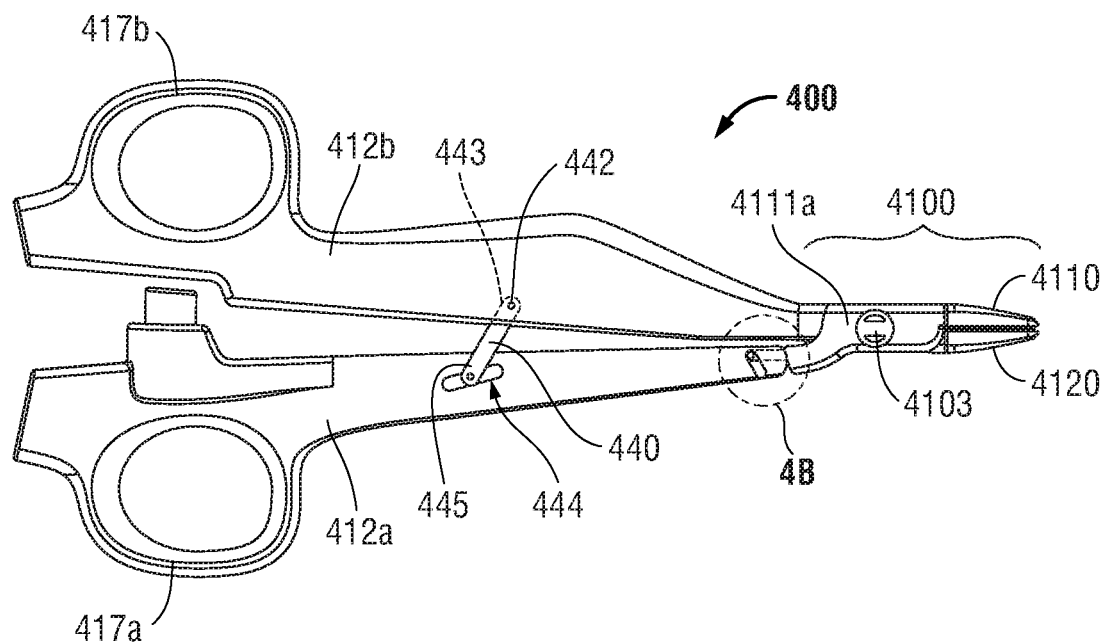
FIG. 4A is a side view of another forceps provided in accordance with the present disclosure, wherein jaw members of the end effector assembly of the forceps are disposed in a closed position.
Figure 4B:
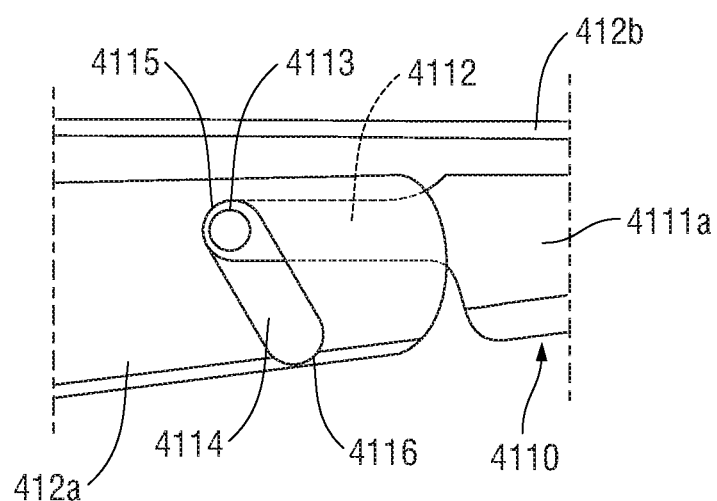
FIG. 4B is a enlarged view of the area of detail indicated as "4B" in FIG. 4A.

With shaft members 412a, 412b disposed in the approximated position and, accordingly, jaw members 4110, 4120 disposed in the closed position, as shown in FIGS. 4A and 4B, transverse pin 4113 is disposed at first ends 415 of angled slots 414 of shaft member 412a such that shaft member 412a is disposed in substantial alignment with proximal flange portion 4111a of jaw member 4110. Further, in the approximated position of shaft members 412a, 412b, linkage 440 is disposed in an angled position.

Figure 4C:
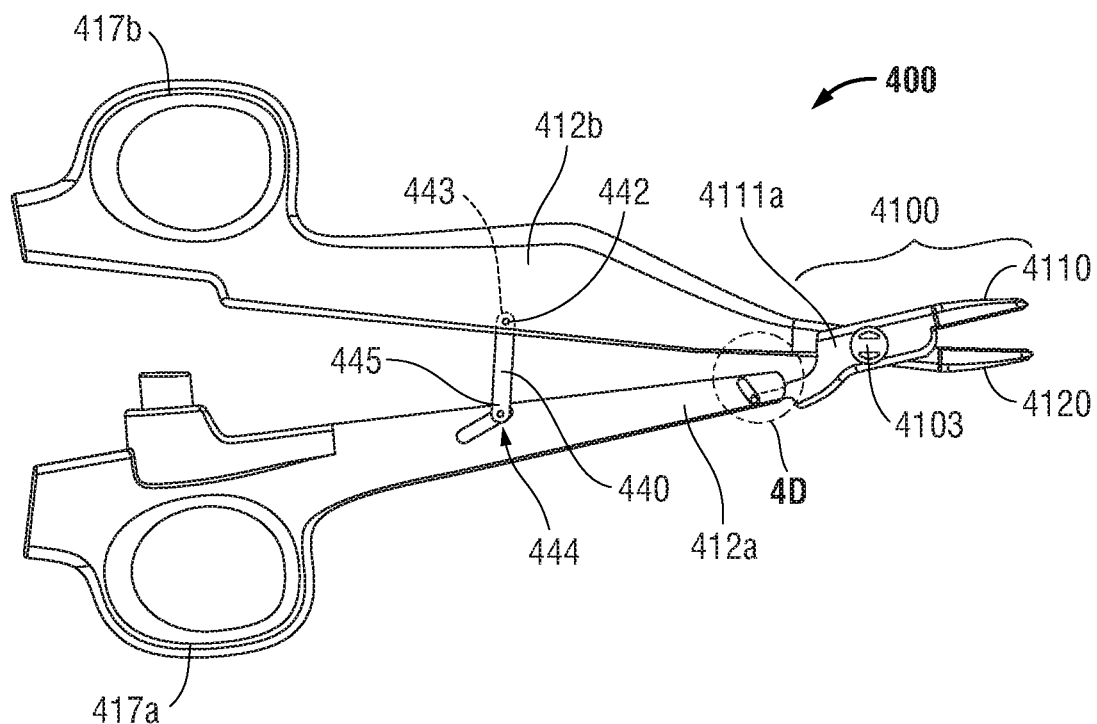
FIG. 4C is a side view of the forceps of FIG. 4A, wherein the jaw member are disposed in an open position.
Figure 4D:
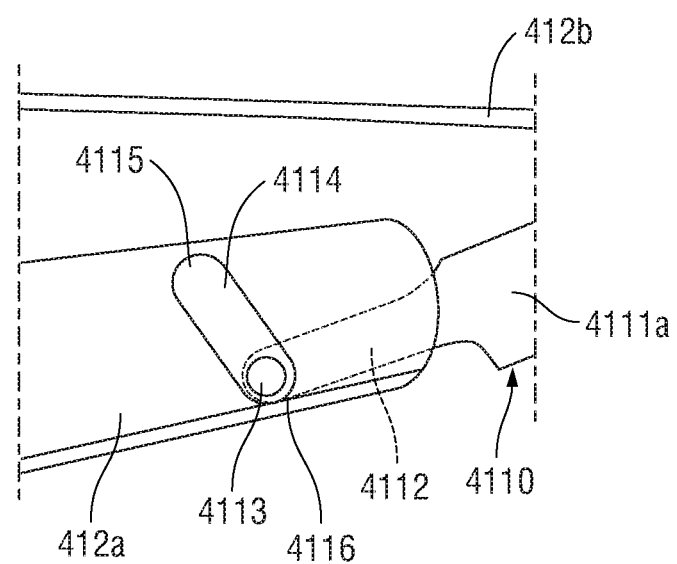
FIG. 4D is a enlarged view of the area of detail indicated as "4D" in FIG. 4C.

In order to move jaw members 4110, 4120 from the closed position (FIG. 4A) to the fully open position (FIG. 4B), the surgeon, with a finger engaged with each handle 417a, 417b, moves shaft members 412a, 412b apart from one another from the approximated position (FIG. 4A) towards the spaced-apart position (FIG. 4B) to pivot jaw members 4110, 4120 from the closed position (FIG. 4A) towards the open position (FIG. 4B). As shaft members 412a, 412b are moved further towards the spaced-apart position, transverse pin 4113 is moved along slots 414 from the first ends 415 thereof (FIG. 4C) towards the second ends 416 thereof (FIG. 4D) such that shaft member 412a is moved relative to proximal flange portion 4111a of jaw member 4110 from the aligned position (FIG. 4C) to an angled position (FIG. 4D), wherein shaft member 412a is offset relative to proximal flange portion 4111a of jaw member 4110 and extends towards shaft member 412b, thereby reducing the distance between handles 417a, 417b and facilitating full opening of jaw members 4110, 4120 (FIG. 4B). In the spaced-apart position of shaft members 412a, 412b, corresponding to the open position of jaw members 4110, 4120, linkage 440 is disposed in a substantially vertical position, as shown in FIG. 4C.

In order to move jaw members 4110, 4120 to the closed position for grasping tissue therebetween, the surgeon moves shaft members 412a, 412b towards one another such that, eventually, transverse pin 4113 is moved along slots 414 from the second ends 416 back to the first ends 415 thereof to return shaft member 412a back to the aligned position, jaw members 4110, 4120 are fully closed, e.g., to grasp tissue therebetween, and linkage 440 is moved back to the angled position.

Figure 5:
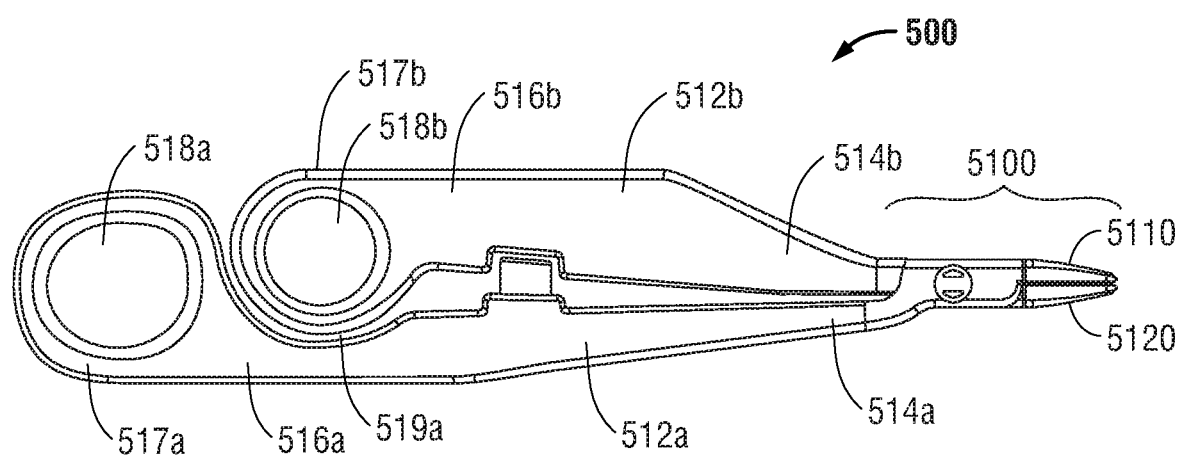
FIG. 5 is a side view of another forceps provided in accordance with the present disclosure.

Turning to FIG. 5, another embodiment of a forceps provided in accordance with the present disclosure is shown generally identified by reference numeral 500. Forceps 500 is shown including two elongated shaft members 512a and 512b and an end effector assembly 5100 including opposing jaw members 5110, 5120 attached to distal ends 514a and 514b of shaft members 512a and 512b, respectively. Shaft members 512a, 512b are pivotable relative to one another between a spaced-apart position and an approximated position to effect movement of jaw members 5110, 5120 relative to one another between an open position and a closed position, respectively, for grasping tissue therebetween.

Each shaft member 512a, 512b of forceps 500 includes a handle 517a, 517b disposed at the proximal end 516a, 516b thereof. Each handle 517a, 517b defines a finger hole 518a, 518b therethrough for receiving a finger of the user. Handles 517a, 517b generally define increased dimensions as compared to the remainder of shaft members 512a, 512b, respectively, such that finger holes 518a, 518b are sufficiently large to permit insertion of a surgeon's finger therethrough. Handles 517a, 517b are configured such that this increased dimension extends inwardly towards the other shaft member 512b, 512a, respectively. That is, the portions of shaft members 512b, 512a adjacent handles 517a, 517b on the outwardly-facing sides thereof do not extend outwardly beyond the outer-most dimensions of shaft members 512a, 512b. As a result of this configuration, finger holes 518a, 518b are positioned closer to one another than can be achieved where at least a portion of either or both of handles 517a, 517b extend outwardly from its respective shaft member 512a, 512b. Similarly as described above, such a feature is advantageous in that it increases the surgeon's ability to move jaw members 5110, 5120 to the fully open position.

However, although the above configuration of handles 517a, 517b facilitates the surgeon's ability to fully open jaw members 5110, 5120, such an inwardly-extending handle 517a, 517b alone would inhibit the ability to fully close jaw members 5110, 5120, e.g., to achieve an appropriate grasping pressure and/or gap distance. As such, handles 517a, 517b of forceps 500 are longitudinally-offset relative to one another. That is, handle 517a is offset proximally relative to handle 517b, thus allowing shaft members 512a, 512b to be fully approximated and, accordingly, allowing jaw members 5110, 5120 to be fully closed. It is also envisioned that this configuration be reversed, e.g., wherein handle 517a is offset distally relative to handle 517b. Further, one or both of shaft members 512a, 512b, e.g., shaft member 512a, may further include a recess 519a shaped complementary or partially-complementary to and configured to receive handle 517b to permit further approximation of shaft members 512a, 512b.

The various embodiments disclosed hereinabove may additionally or alternatively be configured to work with robotic surgical systems and what is commonly referred to as "Telesurgery." Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical forceps, comprising:
   first and second shaft members, each shaft member including a jaw member disposed at a distal end thereof and a handle disposed at a proximal end thereof, the first and second shaft members pivotably coupled to one another towards the distal ends thereof and pivotable relative to one another between a spaced-apart position and an approximated position for moving the jaw members relative to one another between an open position and a closed position to grasp tissue therebetween, the handles of the first and second shaft members extending inwardly towards one another and longitudinally offset relative to one another,
   wherein one of the shaft members defines an inward-facing recess complimentarily-shaped to at least partially receive the longitudinally offset handle of the other shaft member upon movement of the shaft members to the approximated position,
   wherein the first shaft member includes a first outer surface defining a first portion and a second portion, the second portion forming a first obtuse angle with the first portion,
   wherein the second shaft member includes a second outer surface defining a third portion and a fourth portion, the fourth portion forming a second obtuse angle with the third portion, and
   wherein the first obtuse angle is longitudinally offset from the second obtuse angle.

2. The surgical forceps according to claim 1, wherein each shaft member defines an outer dimension along an outwardly-facing side thereof and wherein the handles of the respective shaft members are fully disposed within the respective outer dimensions.

3. The surgical forceps according to claim 1, wherein at least one of the jaw members is adapted to connect to a source of energy for conducting energy through tissue grasped between the jaw members to treat tissue.

4. The surgical forceps according to claim 3, wherein one of the shaft members includes an activation button positioned to oppose the other shaft member such that energy is supplied to the at least one jaw member upon movement of the shaft members to the approximated position.

5. The surgical forceps according to claim 1, wherein at least one of the handles defines a finger hole.

6. The surgical forceps according to claim 1, wherein each of the handles defines a finger hole, the finger holes longitudinally offset relative to one another.

7. A surgical forceps, comprising:
   first and second shaft members, each shaft member including a jaw member disposed at a distal end portion thereof and a handle disposed at a proximal end portion thereof, the first and second shaft members pivotably coupled to one another towards the distal end portions thereof and pivotable relative to one another between a spaced-apart position and an approximated position for moving the jaw members relative to one another between an open position and a closed position to grasp tissue therebetween, the handles of the first and second shaft members each defining a finger hole, the finger holes longitudinally offset relative to one another,
   wherein one of the shaft members defines an inward-facing recess complimentarily-shaped to at least partially receive the longitudinally offset handle of the other shaft member upon movement of the shaft members to the approximated position,
   wherein the first shaft member includes a first outer surface defining a first portion and a second portion, the second portion forming a first obtuse angle with the first portion,
   wherein the second shaft member includes a second outer surface defining a third portion and a fourth portion, the fourth portion forming a second obtuse angle with the third portion, and
   wherein the first obtuse angle is longitudinally offset from the second obtuse angle.

8. The surgical forceps according to claim 7, wherein the handles extend inwardly towards one another.

9. The surgical forceps according to claim 8, wherein each shaft member defines an outer dimension along an outwardly-facing side thereof and wherein the handles of the respective shaft members are fully disposed within the respective outer dimensions.

10. The surgical forceps according to claim 7, wherein at least one of the jaw members is adapted to connect to a source of energy for conducting energy through tissue grasped between the jaw members to treat tissue.

11. The surgical forceps according to claim 10, wherein one of the shaft members includes an activation button positioned to oppose the other shaft member such that energy is supplied to the at least one jaw member upon movement of the shaft members to the approximated position.

12. A surgical forceps, comprising:
first and second shaft members, each shaft member including a jaw member disposed at a distal end portion thereof and a handle disposed at a proximal end portion thereof, the first and second shaft members pivotably coupled to one another towards the distal end portions thereof and pivotable relative to one another between a spaced-apart position and an approximated position for moving the jaw members relative to one another between an open position and a closed position to grasp tissue therebetween, wherein one of the shaft members defines an inward facing recess complimentarily-shaped to at least partially receive the handle of the other shaft member upon movement of the shaft members to the approximated position,
wherein the first shaft member includes a first outer surface defining a first portion and a second portion, the second portion forming a first obtuse angle with the first portion,
wherein the second shaft member includes a second outer surface defining a third portion and a fourth portion, the fourth portion forming a second obtuse angle with the third portion, and
wherein the first obtuse angle is longitudinally offset from the second obtuse angle.

13. The surgical forceps according to claim 12, wherein the handles extend inwardly towards one another.

14. The surgical forceps according to claim 12, wherein the handles are longitudinally offset relative to one another.

15. The surgical forceps according to claim 12, wherein each shaft member defines an outer dimension along an outwardly-facing side thereof and wherein the handles of the respective shaft members are fully disposed within the respective outer dimensions.

16. The surgical forceps according to claim 12, wherein at least one of the jaw members is adapted to connect to a source of energy for conducting energy through tissue grasped between the jaw members to treat tissue.

17. The surgical forceps according to claim 12, wherein one of the shaft members includes an activation button positioned to oppose the other shaft member such that energy is supplied to the at least one jaw member upon movement of the shaft members to the approximated position.

18. The surgical forceps according to claim 12, wherein each of the handles defines a finger hole, the finger holes longitudinally offset relative to one another.

* * * * *